United States Patent
Murata et al.

(10) Patent No.: US 6,348,201 B2
(45) Date of Patent: *Feb. 19, 2002

(54) EXTERNAL COMPOSITION FOR SKIN COMPRISING SPHINGOGLYCOLIPID

(75) Inventors: Katsumi Murata; Takashi Nozawa; Hisako Hara; Michiki Asai; Sachio Wakayama, all of Tokyo (JP)

(73) Assignee: Kibun Food Chemifa Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/084,394

(22) Filed: May 27, 1998

(30) Foreign Application Priority Data

| May 30, 1997 | (JP) | 9-141768 |
| May 30, 1997 | (JP) | 9-141769 |
| May 30, 1997 | (JP) | 9-141770 |
| May 30, 1997 | (JP) | 9-141771 |
| Jan. 21, 1998 | (JP) | 10-00963 |
| Mar. 12, 1998 | (JP) | 10-061749 |

(51) Int. Cl.$^7$ ............................................. A61K 7/00

(52) U.S. Cl. ........................ 424/401; 536/17.9; 514/25; 435/822

(58) Field of Search ........................ 424/401; 536/17.9; 514/25; 435/822

(56) References Cited

U.S. PATENT DOCUMENTS

5,672,693 A * 9/1997 Kawahara .................. 536/17.9

FOREIGN PATENT DOCUMENTS

| EP | 0150712 | 8/1985 |
| EP | 0587288 | 7/1993 |
| EP | 0587288 | * 3/1994 |
| EP | 0699430 | 3/1996 |
| FR | 2679770 | 2/1993 |
| FR | 2718960 | 10/1995 |
| JP | 61286307 | 12/1986 |
| JP | 62-187404 | * 8/1987 |
| JP | 1242690 | 9/1989 |
| JP | 248520 | 2/1990 |
| JP | 4159203 | 6/1992 |
| JP | 539485 | 2/1993 |
| JP | 6157283 | 6/1994 |
| JP | 68007 | 10/1994 |
| JP | 7133217 | 5/1995 |
| JP | 7285827 | 10/1995 |
| WO | 9715274 | 5/1997 |

OTHER PUBLICATIONS

Abstract of Japanese Patent 06,145,189, May 1994.

Abstract of WIPO Patent 97–394191, Apr. 1997.

Yamamoto, A., et al., "Isolation of a Novel Sphingoglycolipid Containing Glucuronic Acid and 2–Hydroxy Fatty Acid from Flavobacterium devorans ATCC 10829." *J. Biochem* 83:1213–1216 (1978).

Yabuuchi, E., et al., "Flavobacterium Devorans ATCC 10829: A Strain of Pseudomonas Paucimobilis," *J. Gen. Appl. Microbiol.* 25:95–107 (1979).

Kawahara, K., et al., "Isolation of an Unusual 'Lipid A' Type Glycolipd from Pseudomonas Paucimobilis," *Biochimica Et Biophysica Acta* 712:571–575 (1982).

Yabuuchi, E., et al., "Proposals of Sphingomonas paucimobilib gen. nov. and comb. nov., Sphingomonas parapaucimobilis sp. nov., Sphingomonas yanikuyae sp. nov., Sphingomonas adhaesiva sp. nov., Sphingomonas capsulate comb. nov., and Two Genospecies of the Genus Sphingomonas," *Microbiol Immunol.* 34–2:99–119 (1990).

\* cited by examiner

*Primary Examiner*—Thurman K. Page
*Assistant Examiner*—Lakshmi Channavajjala
(74) *Attorney, Agent, or Firm*—Browdy and Neimark

(57) ABSTRACT

The present application discloses an external composition for skin comprising a component obtaint by washing a bacterium of the genus Sphingomonas with acetone and then extracting the resultant with alcohol or alcohol-water mixture; an external composition for skin comprising a component extracted from a white bacterium of the genus Sphingomonas; and an external composition for skin comprising a sphingoglycolipid represented by the following formula:

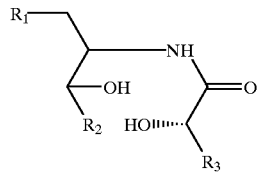

where, $R_1$ represents a sugar portion consisting of a single uronic acid or one to four hexoses selected from a group consisting of uronic acid, glucosamine, galactose and mannose; $R_2$ represents an alkyl group which may have a cycloalkyl group, an alkenyl group or an alkynyl group; and $R_3$ represents an alkyl group; these alkyl, alkenyl and alkynyl groups being straight or branched, and substituted or unsubstituted. These external compositions for skin exhibit excellent moisturizing and skin roughnes prevention effects.

23 Claims, No Drawings

EXTERNAL COMPOSITION FOR SKIN COMPRISING SPHINGOGLYCOLIPID

BACKGROUND OF THE INVENTION

1. Field of the Invention

This invention relates to external compositions for skin comprising sphingoglycolipid available as cosmetic and medicine. The external compositions for skin of the present invention have a potent moisturizing effect and preventive effect against skin roughness.

2. Description of the Related Arts

Skin roughness is caused by losing moisture from the skin surface during dry weather or cleansing. Miscellaneous chemical substances present in modern society can contact skin to inhibit skin functions, which may also result in skin roughness due to depression of lipid secretion ability. It is thus expected to provide external compositions for skin having an excellent moisturizing effect and capable of preventing skin roughness before it occurs.

Various compounds have been proposed as active moisturizers, typified by water-soluble polyol, some of which have already been put into practical use. Many of such moisturizing compounds already put into practical use, however, suffer from uncomfortability upon application or from insufficient moisturizing effect. Thus a new moisturizing compound is still awaited.

In such situation, sphingoglycolipid has been attracting an attention as a safe moisturizing compound.

For example, JP-A-H1-242690, H2-48520, H4-159203 and JP-B-H6-80007 describe that sphingoglycolipid has a skin moisturizing effect. Structures and compositions of the sphingoglycolipids appears in these patent specifications are, however, not clearly disclosed.

JP-A-H6-157283 describes a moisturizing external cutaneous cosmetic containing, as its one component, a sphingoglycolipid represented by a specific general formula. The sugar portion of this general formula is, however, expressed simply as a saccharide residue without mentioning its details.

JP-A-S61-286307 clearly specifies a sphingoglycolipid having a moisturizing effect. This patent describes that ganglioside has skin moisturizing and emollient effects and discloses skin cosmetics containing such ganglioside or its salts. Ganglioside refers to a sphingoglycolipid typically containing neutral sugar, amino sugar and sialic acid.

JP-A-H5-39485, H7-133217 and H7-285827 disclose an external cutaneous remedy using cerebroside. Cerebroside refers to a sphingoglycolipid containing 1 mol each of fatty acid, sphingosine base and neutral sugar (galactose or glucose).

Although several sphingoglycolipids as mentioned above have been known, their moisturizing effects are not always enough to be satisfactory. Cosmetics applied to the skin are also required to exert a preventive effect against skin roughness, as well as a moisturizing effect. But previously-known sphingoglycolipid cannot satisfy the expected preventive effect against skin roughness.

It is thus an object of the present invention to provide an external composition for skin comprising Sphingomonas strain extract having an excellent moisturizing effect and preventive effect against skin roughness. It is another object of the present invention to provide an external composition for skin comprising an extract with a color lighter than that of the previous extracts from Sphingomonas strains. It is another object of the present invention to provide Sphingomonas strains capable of producing such extract with a lighter color. It is still another object of the present invention to identify structures of sphingoglycolipids having potent moisturizing and skin roughness preventive effects and to provide an external composition for skin comprising such glycolipids.

These and other objects will be apparent from the description in the entire part of this specification.

DISCLOSURE OF THE INVENTION

After a series of thorough investigations, the present inventors succeeded in obtaining extracts having potent moisturizing and skin roughness preventive effects by extracting Sphingomonas strain according to a specially designed method, and accomplished the present invention. Thus the first aspect of the invention relates to providing an external composition for skin obtained by washing Sphingomonas strain with acetone, and extracting the resultants with alcohol or alcohol-water mixture. Preferable extracting solutions are methanol, propanol-water mixture or butanol-water mixture. Propanol content in propanol-water mixture is preferably 75 wt % or below. Butanol content in butanol-water mixture is preferably 95 wt % or below, and more preferably 85 to 95 wt %, both ends inclusive.

The second aspect of the invention relates to provide an external composition for skin comprising an extract obtained from white bacteria of the genus Sphingomonas, in particular from *Sphingomonas paucimobilis*. Preferable white bacteria include *Sphingomonas paucimobilis* KFC-W-1; deposition Nos. FERM P-16238 and BP-6368), *Sphingomonas paucimobilis* MK-253W; deposition Nos. FERM P-16693 and BP-6369), *Sphingomonas paucimobilis* MK-254W; deposition No. FERM P-16694 and BP-6370) and *Sphingomonas paucimobilis* MK-332W; deposition No. FERM P-16695 and BP-6371).

The third aspect of the invention relates to an external composition for skin comprising a sphingoglycolipid represented by a formula shown below:

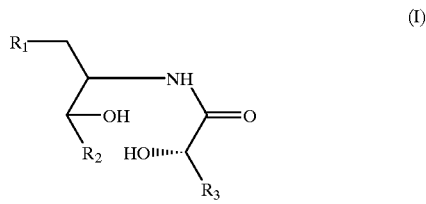

(I)

In the above formula, $R_1$ represents a sugar portion consisting of a single uronic acid or one to four hexoses selected from a group consisting of uronic acid, glucosamine, galactose and mannose; $R_2$ represents an alkyl group which may have a cycloalkyl group, an alkenyl group or an alkynyl group; and $R_3$ represents an alkyl group; these alkyl, alkenyl and alkynyl groups being straight or branched, and substituted or unsubstituted.

$R_1$ preferably consists of three to four hexoses. More preferably, $R_1$ is any one of a four-hexose sugar portion consisting of uronic acid, glucosamine, galactose and mannose; a three-hexose sugar portion consisting of uronic acid, glucosamine, and galactose; or a two-hexose sugar portion consisting of uronic acid and galactose. Still more preferably, $R_1$ is represented by any one of the following formulae:

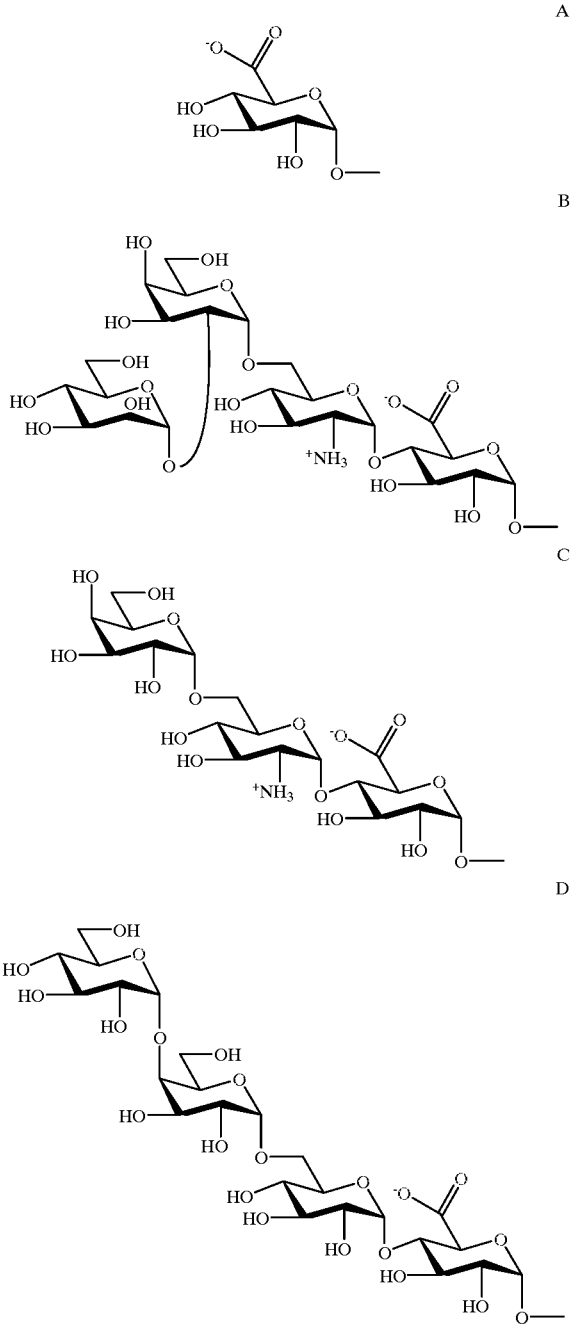

R$_2$ preferably has 15 to 25 carbon atoms, and more preferably has any one of the following structures:

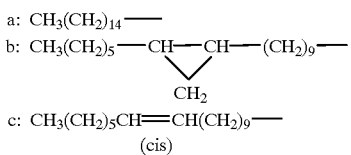

a: $CH_3(CH_2)_{14}$— b: $CH_3(CH_2)_5$—CH—CH—$(CH_2)_9$—
         \  /
         CH$_2$ c: $CH_3(CH_2)_5CH=CH(CH_2)_9$—
(cis)

R$_3$ is preferably a substituted or unsubstituted straight alkyl group having 10 to 20 carbon atoms, and more preferably a straight alkyl group having 10 carbon atoms.

The external composition for skin of the invention is available as for example toilet soap, shampoo, cleansing foam, rinse, eye cream, eye shadow, cream or milky lotion, toilet lotion, perfume, face powder, facial oil, hair-care cosmetics, hair dye, jelly fragrance, powder, pack, shaving cream, shaving lotion, suntan oil, anti-suntan oil, suntan lotion, sun-screening lotion, suntan cream, sun-screening cream, foundation, powdery fragrance, cheek rouge, mascara, eyebrow pencil, nail cream, nail enamel, nail enamel remover, hair cleaner, bath cosmetics, lipstick, lip cream, eyeliner, toothpaste, deodorant agent, eau de cologne, hair tonic, hair restorer, ointment, wet pack, medicated lip cream or anti-atopic agent. The external composition for skin of the invention can contain at least one additive selected from a group consisting of whitening agent, surfactant, dye, perfumery, aseptic agent, pigment, mildew-proof agent, antioxidant, UV absorber, infrared absorber, fluorescent material, metal ion blocker, binder, filler, antiphlogistic, circulation accelerator, cell activator and antibiotic.

DESCRIPTION OF THE PREFERRED EMBODIMENTS

An external composition for skin according to the first aspect of the invention comprises an extract obtained by washing Sphingomonas strain with acetone and successive extraction with alcohol or alcohol-water mixture.

Strains applicable to the present invention belong to the genus Sphingomonas. Strains in the genus Sphingomonas are known for their ability to produce various components including sphingoglycolipid. Any strain is allowable for the present invention provided that it belongs to genus Sphingomonas. Thus any strain in the classifications of *Sphingomonas paucimobilis, Sphingomonas capsulata,* or *Sphingomonas adhaesiva* is available.

Although they are typically listed as *Sphingomonas paucimobilis* FERM BP-3631, *Sphingomonas paucimobilis* FERM BP-3632, *Sphingomonas paucimobilis* FERM BP-3633, *Sphingomonas paucimobilis* FERM BP-3634, *Sphingomonas capsulate* FERM BP-3709 and *Sphingomonas adhaesiva* FERM BP-3710, many other strains in the genus Sphingomonas are used in a similar manner.

The strain can be used either singly or in combination with other strain. Combination and mixing ratio of a plurality of strains is not limited.

To obtain an extracted component, the strain of genus Sphingomonas is first treated with acetone to thoroughly dewater the bacterial body, then the bacterial body is separated by a method, such as filtration. Acetone is most preferably used as a single solvent, but its mixtures with water-base solvent are also allowable. Addition volume of acetone is set between 0.1 to 1000 liters per 1 kg of wet fungus body, and more preferably between 1 to 10 liters.

After the addition of acetone, the contents of the bacterial body is thoroughly brought into contact with acetone. It is also recommendable to apply physical force to the bacterial body to raise the contact efficiency. There is no limitation on a contact duration as far as water in the bacterial body is successfully removed. Generally the duration is set to 20 seconds to 2 hours according to extent of the physical stress. After that the bacterial body is separated from the acetone solution by, for example, filtration.

Separated bacterial body is then extracted with alcohol or alcohol-water mixture. Alcohol used here is selected from hydrocarbon compounds having a hydroxyl group, and preferably from alkanol having 1 to 8 carbon atoms. For use of a single alcohol, preferable ones include methanol, propanol and butanol, where methanol excels the others. Structural isomers of propanol and butanol are also available, where n-propanol, isopropanol, and n-butanol are recommended.

As for use of alcohol-water mixture, propanol-water mixture and butanol-water mixture are preferable. Propanol content in propanol-water mixture is preferably set not higher than 90%, and more preferably not higher than 75%. Butanol content in butanol-water mixture is preferably set not higher than 95%, and more preferably between 80 to 95%.

Extraction using these solvents can comply with a method common in this technical field. For example, extraction is carried out once or repeated several times using approx. 1 to 50 liters of solvent per 1 kg of wet bacterial body.

Obtained extract is then distilled by a known method to remove the solvent to yield a residual syrup. Drying this residual syrup will result in a solid composition. It is also possible to obtain the solid composition by adding acetone to the residual syrup and by collecting the resultant precipitate by filtration or other methods.

Thus-obtained sphingoglycolipid composition possesses excellent moisturizing and skin roughness preventing effects and is confirmed that it can provide appropriate moisture to skin surface to retain its smoothness. Such effects are much more superior to those of ganglioside or galactocerebroside, also both of which are sphingoglycolipid with accepted moisturizing effect.

An external composition for skin according to the second aspect of the invention contains an extract obtained from white bacteria of the genus Sphingomonas.

The white bacteria specified herein refer to those lacking color typically observed in previously-known strains of genus Sphingomonas, or to those appearing lighter even if they have color. The white bacteria are not limited to those the look white by visual observation, but also include those with no color or pale color. Strains with no color are most preferable for the present invention. Such white bacteria have never been found in genus Sphingomonas, and are identified as novel strains.

From another viewpoint, the white bacteria can be referred as strains of genus Sphingomonas having no or little color substance. All of strains of genus Sphingomonas previously known exhibit yellowish color due to their production of carotenoid dyes. On the contrary, the white bacteria are new ones producing no or little carotenoid dyes.

Any strains of white bacteria are available in this invention as far as they belong to genus Sphingomonas. Thus strains of any one of classifications such as *Sphingomonas paucimobilis*, *Sphingomonas capsulata*, and *Sphingomonas adhaesiva* are acceptable.

Typical white bacteria include *Sphingomonas paucimobilis* KFC-W-1; deposition Nos. FERM P-16238 and BP-6368), *Sphingomonas paucimobilis* MK-253W; deposition Nos. FERM P-16693 and BP-6369), *Sphingomonas paucimobilis* MK-254W; deposition No. FERM P-16694 and BP-6370) and *Sphingomonas paucimobilis* MK-332W; deposition No. FERM P-16695 and BP-6371).

These white bacteria are roughly classified into two groups based on their properties. One of these groups is characterized by exhibiting citric acid metabolizing property in Chrinstensen's citric acid agar medium, producing no hydrogen sulfide, and hydrolyzing Tween 20, where KFC-W-1 belongs thereto. Another one is characterized by having no citric acid metabolizing property in Christensen's medium, producing hydrogen sulfide, showing no hydrolysis of Tween 20, where MK-253W, MK-254W and MK-332W belong thereto. Any other white strain which does not belong to the above groups can also be used in this invention.

There is no limitation on a method for obtaining the white strain. Those isolated from plants and soil, or those obtained after mutating conventional strains are both permissible. Obtaining the white strain by mutation can start from a colored strain of genus Sphingomonas whose properties and types are not limited. It is, however, more preferable to start from colored strains which have greater proliferating potential, since in general such colored strains can yield mutants having larger proliferating potential.

The mutant can be obtained by any conventional method for obtaining mutants. It is such that culturing in a medium for a certain period, thoroughly replacing the culture liquor to prepare a new medium, again culturing in the new medium for a certain period, and repeating these steps afterwards. The four above strains were successfully obtained by such method from the eleventh culture liquor containing strains of genus Sphingomonas (IAM 12576) at a probability of $1/10^9$ cells.

A medium used for obtaining such mutant can be selected from a variety of those used generally in bacterial culture. A preferable medium relates to that can help growth of a strain of genus Sphingomonas. Exceptionally preferable one is a mixed medium containing compounds selected from of (1) glucose, (2) yeast extract, and (3) sodium glutamate, L-glutamic acid and glycine. This preferable medium will be described below.

Ratio of contents of individual components in the medium (1):(2):(3) is preferably set at 1:0.3–1.0:0.05–0.5, and more preferably at 1:0.4–0.7:0.1–0.3. Sodium glutamate is a better choice as component (3).

Concentrations of the individual components contained in the medium is set in a concentration range by which strains of genus Sphingomonas will grow well. A preferable concentration range for glucose is between 0.2 and 10 wt %, both ends inclusive. A preferable concentration range for yeast extract is between 0.1 and 10 wt %, both ends inclusive. And a preferable concentration range for a compound selected from a group consisting of sodium glutamate, L-glutamic acid and glycine is between 0.05 and 10 wt %, both ends inclusive.

A good medium is typically expressed as containing 0.5 to 3 wt % of glucose, 0.1 to 1 wt % of yeast extract, and 0.05 to 0.5 wt % of a compound selected from a group consisting of sodium glutamate, L-glutamic acid and glycine. A still more preferable medium is expressed as 0.7 to 1.5 wt % of glucose, 0.3 to 0.7 wt % of yeast extract, and 0.1 to 0.3 wt % of a compound selected from a group consisting of sodium glutamate, L-glutamic acid and glycine.

This medium can contain a small amount of basic inorganic components such as sodium, potassium, calcium, magnesium, phosphorus, and chlorine. A very small amount of other inorganic components, amino acid, vitamin and hormone are also permissible.

There is no special limitation on a carrier of the medium, so that the medium can have any form of solid, semi-solid or liquid. Agar, gelatin and silica gel are also allowable to prepare solid and semi-solid media.

Culture in these media will result in highly efficient proliferation of strains in genus Sphingomonas. The proliferation is much more remarkable than in a case using other media. That is, the strain can proliferate to a greater extent in a shorter time period than in media which have conventionally been used for proliferating or growing strains of genus Sphingomonas. For instance, a medium containing 1.0% glucose, 0.5% yeast extract and 0.2% glutamic acid can give a proliferation potential much greater than that is given by a medium containing 3.0% glucose, 0.1% ammonium chloride, 0.1% ammonium sulfate, 0.05% dipotassium hydrogen phosphate, 0.05% magnesium sulfate heptahydrate, 0.05% potassium chloride and 0.001% iron sulfate heptahydrate. The above medium can also provide a much greater proliferation rate as compared with a case using a medium containing 1.0% glucose, 0.5% yeast extract and 0.2% cassamino acids. Thus the above medium is much advantageous in obtaining a large amount of sphingoglycolipid in a shorter period, since it allows very efficient growth of strains in genus Sphingomonas.

Culture conditions for obtaining the mutant can properly be determined. The culture is generally run at around room temperature to 40° C., and for three hours to one week per run. It is recommended to shake the medium containing the strain using a shaker or so according to the general culture methods.

Using the white bacteria of the invention, it is possible to obtain a white composition containing sphingoglycolipid. The term "white" defined in the invention also covers a compound with a more pale appearance as compared with that of sphingoglycolipid-containing composition derived in a similar manner from colored bacteria. Such white sphingoglycolipid is directly applicable to cosmetic or other products which require aesthetic properties, without being subjected to a decoloring process. In other words, such white sphingoglycolipid contains no coloring component, or even if it does, at a very small and negligible amount, so that any decoloring process needed previously can be abandoned. Thus by using the white bacteria of the invention, white sphingoglycolipid-containing composition is obtained at a good economic efficiency, which promises a large industrial merit.

A method for obtaining the white sphingoglycolipid-containing composition is not limited to a special one. Any usual extraction method is applicable to obtain the sphingoglycolipid-containing composition. Most preferable method relates to that provided according to the first aspect of the invention.

The sphingoglycolipid-containing composition isolated from the white bacteria has an excellent moisturizing effect and skin roughness protection effect, and is confirmed that it can give an appropriate moisture to skin surface to keep its smoothness. Such effects are confirmed to be equal to or higher than those of colored sphigoglycolipid-containing composition obtained from colored bacteria.

The external composition for skin according to the third aspect of the invention is comprises the structure represented by formula (1) shown in the above.

In formula (1), $R_1$ represents a sugar portion consisting of one to four hexoses selected from a group consisting of uronic acid, glucosamine, galactose and mannose, or a single uronic acid. As for one to four hexoses, one to four units are selected from uronic acid, glucosamine, galactose and mannose to be combined, where the number of each hexose, sequence, bond form and optical isomerism are not restricted. Typical combinations of $R_1$ include that having uronic acid as an only hexose; that having one uronic acid, one glucosamine, one galactose and one mannose to be totaled as four hexoses; that having one uronic acid, one glucosamine and one galactose to be totaled as three hexoses; and that having one uronic acid, one galactose and two glucoses to be totaled as four hexoses.

$R_1$ is typically represented by structures A to D as shown in the above.

$R_2$ in formula (1) represents an alkyl group, an alkenyl group or an alkynyl group which may have a cycloalkyl group. Although the number of carbon atoms in $R_2$ is not particularly limited, preferred number resides in a range from 15 to 25, both ends inclusive. The alkyl, alkenyl and alkynyl groups representing $R_2$ are straight or branched, and both of those substituted with a hydroxyl group or so, and unsubstituted are allowable. The alkyl group can include in its chain a cycloalkyl group such as a cyclopropyl group. There is also no limitation on the position of a double bond in the alkenyl group or a triple bond in the alkynyl group.

$R_2$ is typically represented by structures a to c as shown in the above.

$R_3$ represents an alkyl group. $R_3$ is straight or branched, and both of those substituted with a hydroxyl group or so, and unsubstituted are allowable. The alkyl group generally has 1 to 50 carbon atoms, preferably 15 to 25 carbon atoms. $R_3$ is typically referred to a straight alkyl group having 12 carbon atoms.

A group of sphingoglycolipids favorably used for the external composition for skin of the invention can be represented by formula (1) where $R_1$ represents a sugar portion given by structures A, B, C or D; and $R_3$ represents a straight alkyl group having 12 carbon atoms.

Another favorable group of sphingoglycolipids can be represented by formula (1) where $R_2$ is given by structures a, b or c; and $R_3$ represents a straight alkyl group having 12 carbon atoms.

A still more favorable group of sphingoglycolipids can be represented by formula (1) where $R_1$ represents a sugar portion given by structures A, B, C or D; $R_2$ is given by structures a, b or c; and $R_3$ represents a straight alkyl group having 12 carbon atoms.

These sphingoglycolipids given by formula (1) can be included singly in an external composition for skin of the invention, or can be included in combination with two or more of them. For the case with the combination, there is no special limitation on the ratio of contents of individual components.

Sphingoglycolipids of formula (1) are obtained by extracting bacterial body containing sphingoglycolipid. Since sphingoglycolipid is contained in bacterial bodies which belong to the genus Sphingomonas, any bacterial body that belongs to the genus Sphingomonas can yield the sphingoglycolipid given by formula (1) through extraction. The sphingoglycolipid given by formula (1) is insoluble in acetone, so that it is preferable to wash the bacterial body with acetone before extraction. As a solvent used for extracting sphingoglycolipid of formula (1), alcoholic solvent such as methanol, or mixed solvent of polar solvents such as alcoholic solvent admixed with chloroform are preferable in terms of yield. Other solvents will be also acceptable provided that they can solubilize the sphingoglycolipid.

When a mixture of the sphingoglycolipid is obtained, individual components can be separated by a method known in this technical field. Chromatographic method, for example, can completely separate individual sphingoglycolipids having as $R_1$ structure A, structure B, structure C and structure D. When chloroform-methanol mixed solvent is used, individual sphingoglycolipids having structure A, structure D, Structure B and Structure C are eluted in this order, which facilitates the separation. Chromatographic conditions such as types of packed material, eluent, elution velocity, pressure and temperature are adjusted properly. It is also advantageous to prepare a derivative of a certain substance contained in the mixture of the sphingoglycolipid using a reagent that specifically reacts with that substance, and run the separation using chemical or physical properties of such derivative.

Use of *Sphingomonas paucimobilis* generally yields sphingoglycolipids of formula (1) having as $R_1$ structures A and B. Use of Sphingomonas capsulata generally yields sphingoglycolipids of formula (1) having as $R_1$ structures A and C. Use of *Sphingomonas adhaesiva* generally yields sphingoglycolipids of formula (1) having as $R_1$ structure A and D. Thus proper selection of the strain based on these findings will help obtaining desired sphingoglycolipids with a high efficiency.

It is also possible to synthesize Sphingoglycolipid of formula (1) by combining synthetic methods which have previously been known. Individual sphingoglycolipids given by formula (1) can be prepared by, for example, previously synthesizing the sugar and sphingosine portions, and then forming an amide bond therebetween.

The following paragraphs details the external composition for skin commonly provided from the first, second and third aspects of the present invention.

There is no limitation on the morphology of the external composition for skin of the invention. Thus any form of solid, liquid, paste, jelly or powder is acceptable. It is possible to accomplish such forms by, for example, solidification with an aid of gellation agent, dispersion using liquid, solubilization by adding solvent, or pulverization through spray drying.

The external compositions for skin of the invention have excellent moisturizing and skin roughness preventing effects and is confirmed that it can provide appropriate moisture to skin surface to retain its smoothness. That is, the external compositions for skin of the invention can retain the moisture of skin for an extended period. Such effects are much superior to those of gangliosides or galactocerebrosides, also both of which are sphingoglycolipids with accepted moisturizing effect. Thus the external composition for skin of the invention can prove its merits in applications where improvements in skin roughness and keratin conditions, or skin protection is required.

The external composition for skin of the invention also has anti-atopic activity, allowing it to be applied to prevention and therapy of atopic dermatitis.

The external composition for skin of the invention is available, for example, as a cosmetic or medicine. Possible applications include toilet soap, shampoo, cleansing foam, rinse, eye cream, eye shadow, cream or milky lotion, toilet lotion, perfume, face powder, facial oil, hair-care cosmetics, hair dye, jelly fragrance, powder, pack, shaving cream, shaving lotion, suntan oil, anti-suntan oil, suntan lotion, sun-screening lotion, suntan cream, sun-screening cream, foundation, powdery fragrance, cheek rouge, mascara, eyebrow pencil, nail cream, nail enamel, nail enamel remover, hair cleaner, bath cosmetics, lipstick, lip cream, eyeliner, toothpaste, deodorant agent, eau de cologne, hair tonic, or hair restorer. The external composition for skin of the invention can also successfully be used as an ointment or wet pack.

The external composition for skin of the invention can contain various components besides sphingoglycolipids according to purposes of its use. Appropriate components can be added to enhance emollient property, to improve feeling, to reduce dryness after use, to improve solubility, to improve emulsifying property, to improve emulsion stability, to improve compatibility with oily components, to reduce stretched sense after use, to improve adhering to skin, to improve spreadability on skin, to reduce stickiness, to prevent skin roughness, to enhance skin refining effect, to enhance skin protection effect, to improve horny layer, to normalize epidermal keratinization (prevention of partial keratinization due to turnover acceleration, prevention of epidermal thickening, suppression of disorder in epidermal lipid metabolism), to moderate xeroderma such as senile xeroderma, to improve dried skin conditions such as chapping and scaling, to suppress wrinkles formation, to remove wrinkle, to heal wounds, to prevent and improve pigmentation, to delay aging, to reduce dandruff and itch, to relieve depilation, to prevent and heal scalp disease, to improve storability, to retrieve softness, to retrieve flexibility, to provide gloss, to suppress melanin production, and to prevent suntan.

Possible additives for the external compositions for skin of the invention include, for example, oil and fat components, phospholipid, UV absorber, infrared absorber, emulsifier, surfactant, aseptic agent, mildewproof agent, antioxidant, whitening agent, vitamin, amino acid, hormone, peptide, bioactive plant extract, fluorescent material, pigment, dye, perfumery, scrub material, metal ion blocker, binder, filler, thickener, saccharide, nutrient, pH adjuster, chelating agent, sterilizer, keratin conditioner, keratin solubilizer, antibiotic, dermal permeation accelerator, circulation accelerator, antiphlogistic, cell activator, anti-inflammatory, anodyne, emollient agent, skin relaxing agent, traumatic remedy, metabolic accelerator, all of which are compoundable depending on purposes. It is also allowable to add moisturizing components other than active components of the invention.

Oil and fat components compoundable with the external composition for skin of the invention include fatty acids (e.g. oleic acid, behenic acid, isostearic acid, lauric acid, myristic acid, palmitic acid, stearic acid, behenic acid, linoleic acid, γ-linolenic acid, cholumbinic acid, eicosa-(n-6,9,13)-trienic acid, arachidonic acid, α-linolenic acid, Tymnodonic acid, and hexaenic acid), ester oils (e.g. pentaerythritol-tetra-2-ethyl hexanoate, isopropyl myristate, butyl stearate, hexyl laurate, octyldodecyl myristate, diisopropyl adipate and diisopropyl sebacate), waxes (e.g. beeswax, whale wax, lanoline, carnauba wax, candelilla wax and vaseline), animal and plant oils (e.g. mink oil, olive oil, castor oil, cocoa butter, palm oil, cod-liver oil, beef tallow, butter, evening primrose oil rice bran oil and squalane), mineral oils (e.g. hydrocarbon oils and liquid paraffin), silicone oils (e.g. metylphenyl silicone and dimethyl silicone), higher alcohols (e.g. lauryl alcohol, stearyl alcohol, oleyl alcohol, cetyl alcohol, 2-octyl dodecanol and 2-decyltetradecanol) and their derivatives. Allowable organic acids include α-hydroxylic acid, hydroxycarboxylic acid, dicarboxylic acid, glycyrrhizic acid, glycyrrhetinic acid and mevalonic acid (mevalonolactone).

Phospholipids compoundable with the external composition for skin of the invention include glycerophospholipids of the monoacyl ester type or diacyl ester type. They are enumerated as lysophosphatidyl choline, lysophosphatidyl ethanolamine, lysophosphatidyl serine, lysophosphatidyl inositol, phosphatidyl choline, phosphatidyl ethanolamine, phosphatidyl inositol, phosphatidyl serine, phosphatidyl glycerol, phosphatidic acid and sphingomyelin. Natural source lecithin (e.g. yolk) and hydrogenated compounds of the substances listed above are also available.

UV absorbers compoundable with the external compositions for skin of the invention typically include oxybenzone (2-hydroxy-4-methoxybenzophenone), oxybenzonesulfonic acid, oxybenzone-sulfonic acid (trihydrate), guaiazulene, ethylene glycol salicylate, octyl salicylate, dipropylene glycol salicylate, phenyl salicylate, homomentyl salicylate, methyl salicylate, methyl diisopropyl cinnamate, cinoxate (p-methoxycinnamic acid 2-ethoxyethyl ester), di-p-methoxycinnamic acid mono-2-ethyl-hexylacid glyceryl, dihydroxymethoxybenzophenone, dihydroxy-methoxybenzophenone sodium disulfonate, dihydroxybenzophenone, tetrahydroxy-benzophenone, p-aminobenzoic acid, ethyl p-amino-benzoate, glyceryl p-aminobenzoate, amyl p-dimethylbenzoate, 2-ethylhexyl p-aminobenzoate, p-hydroxyanisole, 2-ethylhexyl-p-methoxycinnamate, isopropyl-p-methoxycinnamate, di-isopropyl cinnamate, 2-(2-hydroxy-5-methylphenyl) benzotriazole, sodium hydroxymethoxybenzophenone sulfonate, 4-tert-butyl-4'-methoxybenzoylmethane, 2-ethylhexyl salicylate, glyceryl-p-aminobenzoate, methyl-o-aminobenzoate, 2-hydroxy-4-methoxybenzophenone, amyl-p-dimethylaminobenzoate, 2-phenylbenzoimidazole-5-sulfonate, 2-hydroxy-4-methoxybenzophenoneimidazole-5-sulfonate, 2-hydroxy-4-methoxybenzophenone-5-sulfonate, digalloyltrioleate, p-methoxysilicocarbonate-2-ethoxyethyl, butylmethoxybenzoyl-methane, glyceryl-mono-2-ethylhexanoyl-di-p-methoxy-benzophenone, 2-ethylhexyl-2-cyano-3,3'-diphenylacrylate, 2,2'-dihydroxy-4-methoxybenzophenone, and ethyl-4-bishydroxy-propylamino-benzoate.

Emulsifiers and surfactants compoundable with the external compositions for skin of the invention include nonionic surfactants, anionic surfactants and cationic surfactants.

As the nonionic surfactants enumerated are sorbitan ester (e.g. sorbitan monolaurate, sorbitan monooleate, sorbitan monoisostearate), polyoxyethylene sorbitan ester (e.g. polyoxyethylene sorbitan monoisostearate, polyoxyethylene sobitan monolaurate, polyoxyethylene sorbitan monooleate), glycerol esters (e.g. glycerol monoisostearate, glycerol monomyristate), polyoxyethylene glycerol ether (e.g. polyoxyethylene glycerol monoisostearate, polyoxyethylene glycerol monomyristate), polyglycerin fatty acid ester (e.g. diglyceryl monostearate, decaglyceryl decaisostearate, diglyceryl diisostearate), glycerin fatty acid esters (e.g. glyceryl monocaprate, glyceryl monolaurate, glyceryl monomyristate, glyceryl monopalmitate, glyceryl monooleate, glyceryl monostearate, glyceryl monolinoleate, glyceryl monoisostearate, glyceryl monodilinoleate, glyceryl monodicaprate), polyoxyethyleneglycerin fatty acid esters (e.g. polyoxyethyleneglyceryl monomyristate, polyoxyethyleneglyceryl monooleate, polyoxyethyleneglyceryl monostearate), polyoxyethylene branched alkyl ethers (e.g. polyoxyethylene octyl dodecyl alcohol, polyoxyethylene-2-decyl tetradecyl alcohol), polyoxyethylene alkyl ether (e.g. polyoxyethylene oleyl alcohol ether, polyoxyethylene cetyl alcohol ether), polyoxyethylene hydrogenated castor oil fatty acid ester (e.g. polyoxyethylene hydrogenated castor oil, polyoxyethylene dihydrocholesterol ether, polyoxyethylene hydrogenated castor oil isostearate), and polyoxyethylene alkyl aryl ether (e.g. polyoxyethylene octylphenol ether).

The anionic surfactants are enumerated as salts (e.g. diethanolamine salt, triethanolamine salt, amino acid salt, potassium salt, sodium salt) of higher fatty acids (e.g. oleic acid, stearic acid, isostearic acid, palmitic acid, myristic acid, behenic acid), ethercarboxylic acid alkaline salts, N-acylamino acid salts, N-acylsalcone salts, and higher alkyl sulfonic acid salts.

Typical cationic surfactants and ampholytic surfactants are alkyl quaternary ammonium salts, polyamine, and alkylamine salts.

Powdery agents compoundable with the external compositions for skin of the invention include talc, kaolin, fuller's earth, rubber, starch, silica, silicic acid, aluminum slicate hydrate, chemically modified aluminum magnesium silicate, sodium polyacrylate, tetraalkylaryl snuctite, trialkylarylammonium snuctite, ethylene glycol monostearate, sodium carboxymethylcellulose, carboxyvinyl polymer, chalk, gum, ethylene glycol monostearate, and ethylene glycol distearate.

Polyols compoundable with the external compositions for skin of the invention include polyglycerins such as glycerin, diglycerin, triglycerin or tetraglycerin; ethylene glycol, propylene glycol, 1,3-butylene glycol, 1,4-butylene glycol, dipropylene glycol, polyethylene glycol, sorbitol, erythritol, maltotriose, threitol, sucrose, glucose, maltose, multitose, fructose and xylitose.

Other materials compoundable with the external composition for skin of the invention include vitamins (e.g. vitamin A, vitamin $B_1$, vitamin $B_2$, vitamin $B_6$, vitamin $B_{12}$, vitamin C, vitamin D, vitamin E, vitamin K), amino acids (e.g. proline, leucine, isoleucine, alanine, threonine, lysine, cysteine, arginine), hormones (e.g. estrogen, pregnenolone, adrenal cortex hormone), peptides (e.g. keratin, collagen, elastin), saccharides (those listed above in the section for polyol), inorganic salts (e.g. sodium chloride, sodium hydrogen carbonate, sodium carbonate, borax, sodium sulfate, sodium sulfide, sodium thiosulfate, sodium sesquicarbonate, magnesium oxide, calcium carbonate, magnesium carbonate, potassium chloride, potassium sulfide), cultured lactic acid bacteria, sterols (e.g. cholesterol, provitamin $D_3$, campesterol, stigmastanol, stigmasterol, 5-dihydrocholesterol, α-spinasterol, cholesterol fatty acid ester), sphingosines (e.g. sphingosine, dihydrosphingosine, phytosphingosine, dehydrosphingosine, dehydrophytosphingosine, sphingadienine), ceramide, pseudoceramide, saponin, chitin derivatives, oligosaccharides (e.g. maltose, xylobiose, isomantose, lactose, sucrose, raffinose, maltotriose, xylotriose, maltotetraose, xylotetraose, maltopentaose, xylopentaose, maltohexaose, xylohexaose, maltoheptaose, xyloheptaose), acidic mucopolysaccharides (hyaluronic acid, chondroitin sulfate, dermatan sulfate, heparin, heparan sulfate), and yeast extract.

Still other materials compoundable with the external composition for skin of the invention include thickeners (e.g. carboxyvinyl polymer, carboxymethylcellulose, polyvinyl alcohol, carrageenan, alginate, arginic acid propylene glycol ester, gelatin, electrolytes such as sodium chloride), whitening agent (e.g. arbutin, allantoin, vitamin E derivatives, glycyrrhizin, ascorbic acid phosphoric acid magnesium salt, Kojic acid, panteric acid derivative, placenta extract, coix seed, green tea, pueraria root, mulberry bark, licorice, scutellaria root, aloe, bitter orange peel, *German chamomile, Ganoderma lucidum*), skin protectors (e.g. retinol, retinol ester, retinoic acid), skin emollient agents (e.g. stearyl alcohol, glyceryl monoricinoleate, mink oil, cetyl alcohol, stearic acid, palm oil, castor oil, oxostearic acid), skin relaxing agents (e.g. stearyl alcohol, glycerin monoricinoleate, glycerin monostearate, cetyl alcohol), skin permeation accelerator (e.g. 2-methylpropane-2-ol, 2-propanol, ethyl-2-hydroxypropanoate, 2,5-hexanediol, acetone, tetrahydrofuran), biologically active plant extracts (e.g. extracts from aloe, arnica, licorice, sage or swertia herb), preservatives (e.g. p-hydroxybenzoate, sodium benzoate, urea, metylparaben, ethylparaben, propylparaben, butylparaben), agents (e.g. α-tocopherol, butylhydroxytoluene), buffers (e.g. combination of lactic acid with triethanolamine or sodium hydroxide), keratin solubilizers (e.g. lactic acid, glycolic acid, malic acid, tartaric acid, citric acid), scrubbing materials (e.g. polyethylene powder), and pigments (e.g. lake of calcium, barium or aluminum, iron oxide, titanium dioxide, mica).

It is also possible to add other materials to the external compositions for skin of the invention as required. The amount and method of addition of each component can properly be based on methods known in this technical area.

The external compositions for skin of the invention are widely used in the field where moisturizing and anti-atopic effects are required. The amount of use will be determined so that the desired moisturizing effect is fully achieved.

This invention will be detailed hereinafter referring to the several preferred embodiments. Components, ratios and procedures shown in these embodiments can properly be altered without departing from the spirit of the invention. Thus the scope of the invention is not limited to the following embodiments.

EXAMPLE 1

Obtaining White Bacteria

A medium containing 1.0% glucose, 0.5% yeast extract and 0.2% sodium glutamate (adjusted to pH 7.0 with citric acid) was put into a 500-ml conical flask, and a strain of genus Sphingomonas (IAM 12576) was then added. The content was cultured under shaking using a shaker at 30° C. for 20 hours. The medium was thoroughly removed and another 50 ml of medium with the above composition was newly added, which was again cultured under shaking using a shaker at 30° C. for 20 hours. After repeating such combination of medium exchange and culture ten times, the obtained culture liquor was diluted and sprayed on a plate medium with the above composition. From this culture liquor, *Sphingomonas paucimobilis* KFC-W-1 (Deposition Nos. FERM P-16238 and BP-6368) was found and collected (at a frequency of $1/10^9$ cells).

A similar procedure, except that using a strain of genus Sphingomonas derived from rice plant as an initial strain in place of Sphingomonas strain (IAM 12576), yielded *Sphingomonas paucimobilis* MK-253W (Deposition Nos. FERM P-16693 and BP-6369), a white mutant strain.

A similar procedure, except that using still another strain of genus Sphingomonas derived from rice plant as an initial strain, yielded *Sphingomonas paucimobilis* MK-254W (Deposition Nos. FERM P-16694 and BP-6370), a white mutant strain.

A similar procedure, except that using a strain of genus Sphingomonas derived from Deccan grass as an initial strains yielded *Sphingomonas paucimobilis* MK-332W (Deposition Nos. FERM P-16695 and BP-6371), a white mutant strain.

Obtained white mutant strains and initial strains (IAM 12576) were identified according to "A Guide for Medical Bacterial Identification (3rd edition)". Results were listed in the tables below.

TABLE 1

| Tested Items | S. pauci-mobilis | Initial Strain IAM12576 | KFC W-1 | MK-253W | MK-254W | MK-332W |
|---|---|---|---|---|---|---|
| Mobility | + | + | + | + | + | + |
| Growth at 37° C. | + | + | + | + | + | + |
| Growth at 20–22° C. (25° C.) | + | + | + | + | + | + |
| Brown dye | – | – | – | – | – | – |
| Purple dye | – | – | – | – | – | – |
| Green dye | – | – | – | – | – | – |
| Yellow dye | + | + | – | – | – | – |
| Orange dye | – | – | – | – | – | – |
| Growth on Macconkey's agar | – | – | – | – | – | – |
| Oxidase (kovacs) | d | – | – | – | – | – |
| Oxidation on O-F medium | d | – | – | – | – | – |
| Alkalization on O-F medium | – | – | – | – | – | – |
| Reduction of nitrate to nitrite | – | – | – | – | – | – |
| Simmons' citric acid agar | – | – | – | – | – | – |
| Christen-sen's citric acid agar | d | + | + | – | – | – |
| Urease | – | – | – | – | – | – |
| Gelatinase | – | – | – | – | – | – |
| H₂S | | | | | | |
| (lead acetate paper) | – | – | – | + | + | + |
| (vial tube) | – | – | – | – | – | – |
| Gluconic salt | – | – | – | – | – | – |
| Malonic salt | – | – | – | – | – | – |
| Carbohy-drate, acid; | | | | | | |
| 10% Glucose | – | – | – | – | – | – |
| 10% Galactose Peptone aquamedi-um, acid; | – | – | – | – | – | – |
| Glucose Ammonium salt agar, acid; | – | – | – | – | – | – |
| Glucose | + | + | + | + | + | + |
| Arabinose | + | + | + | + | + | + |
| Cellobiose | + | + | + | + | + | + |
| Ethanol | + | + | + | + | + | + |
| Fructose | + | + | + | + | + | + |
| Glycerin | + | + | + | + | + | + |
| Inositol | – | – | – | – | – | – |
| Galactose | + | + | + | + | + | + |
| Maltose | + | + | + | + | + | + |
| Mannitol | – | – | – | – | – | – |

TABLE 2

| Tested Items | S. pauci-mobilis | Initial Strain IAM12576 | KFC W-1 | MK-253W | MK-254W | MK-332W |
|---|---|---|---|---|---|---|
| Ammonium salt agar, acid; | | | | | | |
| Raffinose | + | + | + | + | + | + |
| Rhamnose | + | + | + | + | + | + |
| Salicin | + | + | + | + | + | + |
| Sorbitol | − | − | − | − | − | − |
| Sucrose | + | + | + | + | + | + |
| Trehalose | + | + | + | + | + | + |
| Xylose | + | + | + | + | + | + |
| Phenylalanine | d | − | − | − | − | − |
| Arginine dihidrase | − | − | − | − | − | − |
| Lysine decarboxylase | − | − | − | − | − | − |
| Ornithine decarboxylase | − | − | − | − | − | − |
| Selenic salt reduction | − | − | − | − | − | − |
| Casein hydrolysis | − | − | − | − | − | − |
| DNase (HCl method) | + | + | + | + | + | + |
| Thornley arginine | − | − | − | − | − | − |
| Tween 20 hydrolysis | + | + | + | − | − | − |
| Tyrosine hydrolysis | + | + | + | + | + | + |
| Brown dye production on tyrosine agar medium | d | + | + | + | + | + |
| Nitrite reduction | − | − | − | − | − | − |
| Growth on PHBA | + | + | + | + | + | + |
| Endogenous PHBA accumulation | + | + | + | + | + | + |
| Fluorescent dye production - King B agar | − | − | − | − | − | − |
| Growth at 5° C. | − | − | − | − | − | − |
| Growth at 42° C. (40° C.) | d | − | − | − | − | − |
| 3-Keto-lactose production | − | − | − | − | − | − |
| Lecithinase | − | − | − | − | − | − |
| Starch hydrolysis | d | + | + | + | + | + |
| Christensen's urea | − | − | − | − | − | − |
| Acylamidase | − | − | − | − | − | − |
| Indole production | − | − | − | − | − | − |
| Acetyl-methyl-carbinol production | − | − | − | − | − | − |

EXAMPLE 2
Proliferation Tests Using Various Media

Various media shown in the table below were adjusted to pH 7.0 using citric acid, which was followed by sterilization. *Sphingomonas paucimobilis* KFC-W-1 was then cultured in these media at 30° C. under shaking using a shaker. Status of bacteria proliferation was confirmed after 24 hours.

TABLE 3

| Medium No. | Glucose | Yeast extract | Sodium Glutamate | Other components |
|---|---|---|---|---|
| 1 | 1.0 | 0.5 | 0.2 | None |
| 2 | 1.0 | — | — | None |
| 3 | — | 1.0 | — | None |
| 4 | — | — | — | 1.0 Peptone |
| 5 | — | — | — | 1.0 Meat extract |
| 6 | — | — | 1.0 | None |
| 7 | — | — | 0.5 | None |
| 8 | 1.0 | — | 0.2 | None |
| 9 | 1.0 | — | — | 0.5 NH$_4$Cl |
| 10 | 1.0 | — | — | 0.2 (NH$_4$)$_2$SO$_4$ |
| 11 | 3.0 | — | — | 0.1 NH$_4$Cl |
|  |  |  |  | 0.1 (NH$_4$)$_2$SO$_4$ |
|  |  |  |  | 0.05 K$_2$HPO$_4$ |
|  |  |  |  | 0.05 MgSO$_4$.7H$_2$O |
|  |  |  |  | 0.05 KCl |
|  |  |  |  | 0.001 FeSO$_4$.7H$_2$O |
| 12 | 1.0 | 0.5 | — | 0.5 Casamino acids |
|  |  |  |  | 0.2 (NH$_4$)$_2$SO$_4$ |
|  |  |  |  | 0.1 MgSO$_4$ |
|  |  |  |  | 0.2 K$_2$HPO$_4$ |

(Unit: wt %)

No significant proliferation of bacteria was observed for media 2, 6, 7, 8, 9 and 10. Medium 11 showed a small extent of proliferation, and media 3, 4 and 5 exceeded it. A still larger extent of proliferation was observed for medium 12, whereas medium 1 showed an exceptionally large extent of proliferation apparently exceeding all of the others.

Same experiments in media 1 having its sodium glutamate concentration altered to 0.1%, 0.5% or 0.8%, respectively, showed that the 0.1% medium can allow proliferation as large as that attained by the 0.2% medium.

Sodium glutamate in medium 1 was then replaced with L-ornithine hydrochloride, glycine, L-leucine, L-methionine, L(+)-lysine hydrochloride, L-cyctein hydrochloride hydrate, L-glutamic acid, L-tryptophan and DL-phenylalanine, respectively, and again similar experiments were performed. It was observed that glycine and L-glutamic acid can cause a proliferation at a level comparable to that for sodium glutamate.

EXAMPLE 3

Preparation of Sphingoglycolipid-Containing Composition

The white bacteria obtained as decribed in Example 1 were cultured at room temperature for 24 hours. The culture was run using a medium containing 1.0% glucose, 0.5% yeast extract and 0.2% sodium glutamate (adjusted to pH7.0 with citric acid) under aeration at 0.7 vvm.

After sterilizing the resulted culture liquor and adjusting its pH at 5.0, the bacterial bodies were collected by centrifugation. Twenty kg of the bacterial bodies were then added to 30 liters of acetone, stirred, and collected by filtration. Thus obtained bacterial bodies were extracted three times with 30 liters each of acetone, and resultant extracts were distilled using a flash evaporator to remove the solvent. Four liters of residual liquor is added with 8 liters of acetone, stirred, and allowed to stand for precipitation. The precipitate was collected, added with another 2 liters of acetone, and again allowed to stand to produce the precipitate. The precipitate was finally collected, dewatered, and dried under reduced pressure to prepare the white composition comprising sphingoglycolipid.

EXAMPLE 4

Preparation of Sphingoglycolipid-Containing Composition

*Sphingomonas paucimobilis* (IAM12576) was cultured at room temperature for 24 hours. The culture was run using a medium containing 1.0% glucose, 0.5% yeast extract and 0.2% sodium glutamate (adjusted to pH7.0 with citric acid) under aeration at 0.7 vvm.

After sterilizing the resulted culture liquor and adjusting its pH at 5.0, the bacterial bodies were collected by centrifugation. Twenty kg of the fungus body was then added with 30 liters of acetone, stirred, and collected by filtration. Thus obtained bacterial bodies were extracted three times with 30 liters each of solvent shown in Table 4, and the resultant extracts were distilled using a flash evaporator to remove the solvent. Four liters of residual liquor is added with 8 liters of acetone, stirred, and allowed to stand for precipitation. The precipitate was collected, added with another 2 liters of acetone, and again allowed to stand to produce the precipitate. The precipitate was finally collected, dewatered, and dried under reduced pressure to prepare the composition comprising sphingoglycolipid (Samples 1 to 19).

TABLE 4

| Sample No. | Solvents | Mixing ratio |
|---|---|---|
| 1 | Methanol | |
| 2 | Methanol/water | 85/15 |
| 3 | Methanol/water | 70/30 |
| 4 | Methanol/water | 55/45 |
| 5 | Ethanol | |
| 6 | Ethanol/water | 85/15 |
| 7 | Ethanol/water | 70/30 |
| 8 | Ethanol/water | 55/45 |
| 9 | Propanol | |
| 10 | Propanol/water | 85/15 |
| 11 | Propanol/water | 70/30 |
| 12 | Propanol/water | 55/45 |
| 13 | Isopropanol | |
| 14 | Isopropanol/water | 85/15 |
| 15 | Isopropanol/water | 70/30 |
| 16 | Isopropanol/water | 55/45 |
| 17 | Butanol | |
| 18 | Butanol/water | 85/15 |
| 19 | Methanol/chloroform | 75/25 |

Findings from a compositional analysis of sphingoglycolipid of Sample 1 are shown in Table 5.

TABLE 5

| Components | Values |
|---|---|
| Heavy metal | 20 ppm or less |
| Arsenic | 2 ppm or less |
| Acid value | 30 or less |
| Iodine value | 20 to 30 |
| Sphingosine | 13.0 to 18.0 |

EXAMPLES 5–25

Production of External Compositions for Skin

As the active components used in the following Examples 5 to 25, sphingoglycolipid-containing compositions prepared in Examples 3 and 4, and at least one active component selected from a group listed below (represented by formula (1) where $R_3$ for all the components is a straight alkyl group having 12 carbon atoms).

TABLE 6

| Active component | $R_1$ | $R_2$ | weight part |
|---|---|---|---|
| 1 | A | a | 1.00 |
| 2 | A | b | 1.00 |
| 3 | A | c | 1.00 |
| 4 | B | a | 1.00 |
| 5 | B | b | 1.00 |
| 6 | B | c | 1.00 |
| 7 | C | a | 1.00 |
| 8 | C | b | 1.00 |
| 9 | C | c | 1.00 |
| 10 | D | a | 1.00 |
| 11 | D | b | 1.00 |
| 12 | D | c | 1.00 |
| 13 | A | a | 0.50 |
|  | A | b | 0.50 |
| 14 | B | a | 0.50 |
|  | B | b | 0.50 |
| 15 | A | a | 0.50 |
|  | B | a | 0.50 |
| 16 | A | b | 0.50 |
|  | B | b | 0.50 |
| 17 | A | a | 0.25 |
|  | B | a | 0.25 |
|  | C | a | 0.25 |
|  | D | a | 0.25 |
| 18 | A | b | 0.25 |
|  | B | b | 0.25 |
|  | C | b | 0.25 |
|  | D | b | 0.25 |
| 19 | A | a | 0.45 |
|  | A | b | 0.45 |
|  | A | c | 0.10 |
| 20 | B | a | 0.45 |
|  | B | b | 0.45 |
|  | B | c | 0.10 |
| 21 | C | a | 0.20 |
|  | C | b | 0.40 |
|  | C | c | 0.40 |
| 22 | D | a | 0.20 |
|  | D | b | 0.40 |
|  | D | c | 0.40 |

EXAMPLE 5

Production of a Toilet Milky Lotion

A first liquid prepared by mixing individual components listed below at 75° C. was added to a second liquid prepared by mixing individual components listed below at 75° C., and then thoroughly emilsified at 75° C. to produce a toilets milky lotion.

TABLE 7

| Components | weight part |
|---|---|
| (First liquid) | |
| Squalane | 4.9 |
| Monostearic acid | 1.8 |
| Vaseline | 1.2 |
| Butylparaben | 0.1 |
| Liquid paraffin | 5.0 |
| (Second liquid) | |
| Active component | 1.0 |
| Sodium cetylsulfate | 0.8 |

TABLE 7-continued

| Components | weight part |
|---|---|
| Methylparaben | 0.2 |
| Purified water | 85.0 |

EXAMPLE 6

Production of a Toilet Lotion

Individual components listed below were mixed at room temperature and thoroughly stirred to produce a toilet lotion.

TABLE 8

| Components | weight part |
|---|---|
| Active component | 1.0 |
| Methylparaben | 0.1 |
| Polyoxyethylene hydrogenated castor oil | 1.2 |
| Polyoxyethylene sorbitol oleate | 0.4 |
| Ethanol | 5.3 |
| Purified water | 92.0 |

EXAMPLE 7

Production of a Powder Foundation

Individual components listed below were mixed at room temperature and thoroughly stirred to produce a powder foundation.

TABLE 9

| Components | weight part |
|---|---|
| Active component | 1.0 |
| Mica | 37.8 |
| Talc | 20.0 |
| Titanium dioxide | 12.0 |
| Kaolin | 5.0 |
| Iron oxide | 3.5 |
| Powdered Nylon | 8.0 |
| Octyldodecyl myristate | 2.0 |
| Neopentylglycol diisooctate | 2.0 |
| Sorbitol monooleate | 0.5 |
| Zinc stearate | 1.0 |
| Red oxide | 1.0 |
| Squalane | 6.0 |
| Aseptic agent | 0.1 |
| Antioxidant | 0.1 |

EXAMPLE 8

Production of a Whitening Powder

Individual components listed below were mixed and ground at room temperature to produce a whitening powder.

TABLE 10

| Components | weight part |
|---|---|
| Active component | 20.0 |
| Sucrose | 50.0 |
| Polyethylene glycol | 10.0 |
| Silica | 4.5 |
| Vitamin C | 5.0 |

TABLE 10-continued

| Components | weight part |
|---|---|
| Vitamin C dipalmitate | 10.0 |
| Dye | 0.5 |

EXAMPLE 9

Production of an Emollient Cream

From the components listed below, 1,3-butylene glycol and purified water were first mixed and heated to 70° C., to which a molten mixture of the residual components was added, which was followed by homogenizing the emulsified particles using a homomixer and cooled to produce a emollient cream.

TABLE 11

| Components | weight part |
|---|---|
| Active component | 5.0 |
| Stearyl alcohol | 6.0 |
| Stearic acid | 2.0 |
| Hydrogenated lanoline | 4.0 |
| Squalane | 9.0 |
| Octyldodecanol | 10.0 |
| POE(25)cetyl alcohol ether | 3.0 |
| glycerin monostearate | 2.0 |
| 1,3-butylene glycol | 10.0 |
| Dye | 0.5 |
| Aseptic agent | 0.1 |
| Antioxidant | 0.1 |
| Purified water | 48.3 |

EXAMPLE 10

Production of a Pre-Shaving Lotion

Individual components listed below were mixed at room temperature and thoroughly stirred to produce a pre-shaving lotion.

TABLE 12

| Components | weight part |
|---|---|
| Active component | 1.0 |
| Zinc sulfophenolate | 1.0 |
| Isopropylmyristic acid ester | 7.0 |
| Isopropylpalmitic acid ester | 8.0 |
| Ethanol | 82.5 |
| Perfume | 0.5 |

EXAMPLE 11

Production of a Cleansing Foam

From the components listed below, palmitic acid, myristic acid, lauric acid, palm oil and aseptic agent were melted by heating and kept at 70° C., to which a mixture of potassium hydroxide and purified water was added, which was followed by adding the residual components and thorough stirring, to produce a cleansing foam.

TABLE 13

| Components | weight part |
| --- | --- |
| Active component | 4.5 |
| Stearic acid | 10.0 |
| Palmitic acid | 10.0 |
| Myristic acid | 12.0 |
| Lauric acid | 4.0 |
| Palm oil | 2.0 |
| Potassium hydroxide | 6.0 |
| Glycerol monostearic acid ester | 2.0 |
| POE(20) Sorbitol monostearate | 2.0 |
| Dye | 0.5 |
| Aseptic agent | 0.1 |
| Chelating agent | 0.2 |
| Purified water | 46.7 |

EXAMPLE 12

Production of a Pack

From the components listed below, titanium oxide and talc were thoroughly dispersed in purified water, to which sorbitol was added and heated to 70° C. to be dissolved, then the residual components were added and thoroughly stirred, which was followed by degassing and cooling to produce a pasty pack.

TABLE 14

| Components | weight part |
| --- | --- |
| Active component | 4.5 |
| Polyvinyl acetate emulsion | 15.0 |
| Polyvinyl alcohol | 10.0 |
| Jojoba oil | 2.0 |
| Squalane | 2.0 |
| POE sorbitol monostearic acid ester | 1.0 |
| Titanium oxide | 5.0 |
| Talc | 10.0 |
| Sorbitol | 10.0 |
| Ethanol | 8.0 |
| Dye | 0.5 |
| Aseptic agent | 0.2 |
| Purified water | 31.8 |

EXAMPLE 13

Production of a Lipstick

Individual components listed below previously heated at 70° C. were mixed, thoroughly stirred, poured into a mold and cooled rapidly to produce a lipstick.

TABLE 15

| Components | weight part |
| --- | --- |
| Active component | 2.0 |
| Castor oil | 25.0 |
| Cetyl 2-Ethylhexanate | 20.0 |
| Lanoline | 10.0 |
| Isopropylmyristic acid ester | 10.0 |
| Candelilla wax | 9.0 |
| Solid paraffin | 8.0 |
| Carnauba wax | 5.0 |
| Beeswax | 5.0 |
| Titanium dioxide | 5.0 |
| Dye | 1.0 |

EXAMPLE 14

Production of a Lip Cream

From the components listed below, active component, stearic acid, stearyl alcohol and butyl stearate, each of which was previously heated to 70° C., were mixed together, the residual components were added, and thoroughly stirred to produce a lip cream.

TABLE 16

| Components | weight part |
| --- | --- |
| Active component | 4.0 |
| Stearic acid | 14.0 |
| Stearyl alcohol | 8.0 |
| Butyl stearate | 10.0 |
| Propylene glycol | 10.0 |
| Glycerin monostearate | 4.0 |
| Potassium hydroxide | 1.0 |
| Antioxidant | 0.2 |
| Purified water | 48.8 |

EXAMPLE 15

Production of a Cheek Rouge

Individual components listed below, except perfume and liquid paraffin, were mixed at room temperature, then the mixture was sprayed with the perfume and the liquid paraffin, which was followed by grinding and compression molding to produce a cheek rouge.

TABLE 17

| Components | weight part |
| --- | --- |
| Active component | 1.5 |
| Talc | 77.8 |
| Kaolin | 9.0 |
| Zinc myristate | 5.0 |
| Pigment | 3.0 |
| Liquid paraffin | 3.0 |
| Perfume | 0.5 |
| Aseptic agent | 0.2 |

EXAMPLE 16

Production of an Eyeliner

From the components listed below, carbon black previously ground was dispersed in purified water, the residual components were added, and the mixture was stirred at room temperature to produce an eyeliner.

TABLE 18

| Components | weight part |
| --- | --- |
| Active component | 10.0 |
| Carbon black | 5.0 |
| Polyoxyethylene dodecyl ether | 2.0 |
| Dye | 0.5 |
| Aseptic agent | 0.2 |
| Purified water | 82.3 |

EXAMPLE 17

Production of a Mascara

From the components listed below, purified water and polyacrylic acid ester emulsion were mixed at 70° C., the residual components previously mixed by heating at 70° C. were then added, which was followed by emulsifying dispersion to produce a mascara.

TABLE 19

| Components | weight part |
|---|---|
| Active component | 4.5 |
| Iron oxide | 10.0 |
| Polyacrylic acid ester emulsion | 27.0 |
| Liquid paraffin | 8.0 |
| Lanoline wax | 8.0 |
| Lightweight isoparaffin | 28.0 |
| Sorbitol sesquioleate | 4.0 |
| Dye | 0.5 |
| Antioxidant | 0.1 |
| Aseptic agent | 0.1 |
| Purified water | 9.8 |

EXAMPLE 18

Production of an Eyebrow Pencil

Individual components listed below except powdery ones were melted and mixed, then the powdery components were added, which was followed by kneading and molding to produce an eyebrow pencil.

TABLE 20

| Components | weight part |
|---|---|
| Active component | 1.0 |
| Iron oxide | 19.0 |
| Titanium oxide | 5.0 |
| Talc | 10.0 |
| Kaolin | 15.0 |
| Japan tallow | 20.0 |
| Stearic acid | 10.0 |
| Beeswax | 5.0 |
| Hydrogenated castor oil | 5.0 |
| Vaseline | 4.0 |
| Lanoline | 3.0 |
| Liquid paraffin | 2.8 |
| Antioxidant | 0.1 |
| Aseptic agent | 0.1 |

EXAMPLE 19

Production of a Hand Cream

Individual components listed below were mixed by heating at 70° C., then thoroughly stirred to produce a hand cream.

TABLE 21

| Components | weight part |
|---|---|
| Active component | 3.0 |
| Glycerin | 20.0 |
| Urea | 2.0 |
| Stearic acid monoglyceride | 2.5 |
| Vaseline | 6.0 |
| Liquid paraffin | 10.0 |
| Purified water | 56.5 |

EXAMPLE 20

Production of a Hair Shampoo

Individual components listed below were mixed by heating at 70° C., then thoroughly stirred to produce a hair shampoo.

TABLE 22

| Components | weight part |
|---|---|
| Active component | 5.0 |
| Glycerin | 1.0 |
| Sodium laurylpolyoxyethylene sulfate | 10.0 |
| Sodium lauryl sulfate | 6.0 |
| Palm oil fatty acid diethanolamide | 3.0 |
| Metal ion blocker | 0.1 |
| pH Adjuster | 0.5 |
| Aseptic agent | 0.2 |
| Purified water | 74.2 |

EXAMPLE 21

Production of a Hair Rinse

Individual components listed below were mixed by heating at 70° C., then thoroughly stirred to produce a hair rinse.

TABLE 23

| Components | weight part |
|---|---|
| Active component | 3.0 |
| Silicone oil | 2.8 |
| Liquid paraffin | 1.2 |
| Glycerin | 2.5 |
| Cetyl alcohol | 1.3 |
| Stearyl alcohol | 1.1 |
| Stearyl chloride trimethylammonium | 0.6 |
| Dye | 1.0 |
| Aseptic agent | 0.2 |
| Purified water | 86.3 |

EXAMPLE 22

Production of a Hair Liquid

Individual components listed below were mixed at room temperature to produce a hair liquid.

TABLE 24

| Components | weight part |
|---|---|
| Active component | 1.0 |
| Polyoxypropylene butyl ether | 20.0 |
| Polyoxyethylene hardened castor oil | 1.0 |
| Ethyl alcohol | 50.0 |
| Perfume | 0.5 |
| Purified water | 27.5 |

EXAMPLE 23

Production of a Hair Dye

Individual components listed below were mixed at room temperature to produce a hair dye.

TABLE 25

| Components | weight part |
|---|---|
| Active component | 3.0 |
| Pigment | 1.0 |
| Acrylic resin alkanolamine (50%) | 8.0 |
| Perfume | 0.5 |
| Ethyl alcohol | 88.0 |

EXAMPLE 24

Production of Bath Salts

Individual components listed below were mixed at room temperature to produce bath salts.

TABLE 26

| Components | weight part |
| --- | --- |
| Active component | 10 |
| Sodium sulfate | 50 |
| Sodium hydrogencarbonate | 25 |
| Sodium chloride | 13 |
| Dye | 2 |

EXAMPLE 25

Production of an Anti-Atopic Ointment

Individual components listed below were emulsified and dispersed at 70° C., and cooled to produce an anti-atopic ointment.

TABLE 27

| Components | weight part |
| --- | --- |
| Composition of Example 7 | 3.0 |
| Vaseline | 24.0 |
| Stearyl alcohol | 21.0 |
| Propylene glycol | 13.0 |
| Polyoxyethylene hardened castor oil | 3.5 |
| Glycerin monostearate | 1.0 |
| Aseptic agent | 0.2 |
| Purified water | 34.3 |

TEST EXAMPLE

Test for Evaluating Moisturizing and Skin Roughness Prevention Effects

Twenty male hairless mice of 9-week old (Skh:hr-1, Nihon SLC) were treated with 0.5% Triton X-150 (50 µl) in a circular area of 2.5 cm diameter on their rear backs. The once-a-day application was continued for 5 days. On the 6th day and thereafter, middle-wavelength UV light was irradiated at a dose of 0.15 J/cm$^2$ using a SE lamp (manufactured by Toshiba Medical Instruments Co., Ltd.), and Samples 1 to 5 (dissolved in 0.5% Triton X-150) listed below and control sample (0.5% Triton X-150) were applied. These procedures were followed once a day and continued up to the 10th day. Five hairless mice were subjected to each test for Samples or the control.

TABLE 28

| Sample No. | Active component | Concentration of active component |
| --- | --- | --- |
| Sample 1 (invention) | No. 19 in Table 6 | 1.0% |
| Sample 2 (invention) | No. 20 in Table 6 | 0.1% |
| Sample 3 (comparison) | Glyceroglycolipid | 1.0% |
| Sample 4 (comparison) | Ganglioside | 1.0% |
| Sample 5 (comparison) | Galactocerebroside | 1.0% |

After the middle-wavelength UV irradiation and the sample application were completed on the 10th day, amount of transcutaneous transpiration was measured using a hydrograph (model AMU-3: manufactured by Fauchon Co., Ltd.) to determine an average value for the five mice. Results were shown in the table below, where the values are expressed in relative values assuming the control (9 g/m$^2$/h) as 100.

TABLE 29

| Sample No. | Relative transcutaneous transpiration |
| --- | --- |
| Control | 100 |
| Sample 1 (invention) | 64 |
| Sample 2 (invention) | 79 |
| Sample 3 (comparison) | 123 |
| Sample 4 (comparison) | 89 |
| Sample 5 (comparison) | 91 |

From these findings, it was made clear that the Samples of this invention allow only quite a low level of transcutaneous transpiration, proving their excellent moisture retaining effect. In the visual observation of the rear backs of the hairless mice after the completion of 10-day tests, there was no sign of skin roughness by the application of the Samples of the present invention unlike the comparative Samples.

These potent moisturizing and skin roughness preventing effects were observed also for other compositions not described in the above Examples. In particular, a sphingoglycolipid prepared from each white bacterium according to the method described in Example 3, and Samples 1, 11, 12, 15, 16 and 18 prepared according to the method described in Example 4 showed exceedingly potent moisturizing and skin roughness preventing effects.

What is claimed is:

1. An external composition for skin comprising a component extracted from a white bacterium of the genus Sphingomonas, said extract being substantially uncolored, wherein said component is obtained by washing said white bacterium of the genus Sphingomonas with acetone, and then extracting the resultant with alcohol or alcohol-water mixture.

2. An external composition for skin according to claim 1 wherein said component extracted from a white bacterium of the genus Sphingomonas comprises a sphingoglycolipid represented by the following formula:

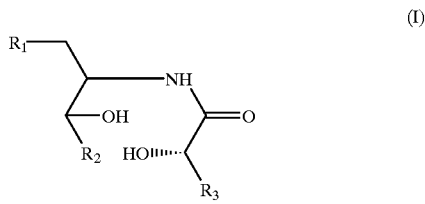

(I)

where, $R_1$ represents a sugar portion consisting of a single uronic acid or one to four hexoses selected from a group consisting of uronic acid, glucosamine, galactose and mannose; $R_2$ represents an alkyl group which may have a cycloalkyl group, an algenyl group or an alkynyl group; and $R_3$ represents an alkyl group; these alkyl, algenyl and alkynyl groups being straight or branched, and substituted or unsubstituted.

3. A method of using said external composition for skin as claimed in claim 1 as a toilet soap, shampoo, cleansing foam, rinse, eye cream , eye shadow, cream or milky lotion, toilet lotion, perfume, face powder, facial oil, hair-care cosmetics, hair dye, jelly fragrance, powder, pack, shaving cream, shaving lotion, suntan oil, anti-suntan oil, suntan lotion, sun-screening lotion, suntan cream, sun-screening cream, foundation, powdery fragrance, cheek rouge, mascara, eyebrow pencil, nail cream, nail enamel, nail enamel remover, hair cleaner, bath cosmetics, lipstick, lip cream, eyeliner, toothpaste, deodorant agent, eau de cologne, hair tonic, hair restorer, ointment, wet pack, medicated lip cream or anti-atopic agent, comprising applying said composition to skin, hair or fingernails.

4. The method of claim 3 wherein said sphingoglycolipid extracted from a white bacterium of the genus Sphingomonas is represented by the formula

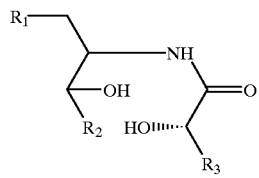

wherein $R_1$ represents a sugar portion of four hexoses consisting of a uronic acid, a glucosamine, a galactose and a mannose; three hexoses consisting of a uronic acid, a glucosamine and a galactose; or four hexoses consisting of a uronic acid, a galactose and two glucoses;

$R_2$ represents an alkyl group which may have a cycloalkyl group, an algenyl group or an alkynyl group; and $R_3$ represents an alkyl group; these alkyl, algenyl and alkynyl groups being straight or branched, and substituted or unsubstituted.

5. The method of claim 4 wherein said composition is a toilet soap, shampoo, cleaning foam or shaving cream.

6. The method of claim 4 wherein said composition further comprises a sunscreen, and said composition is a suntan oil, an anti-suntan oil, a suntan lotion, a sun-screening lotion, a suntan screen or a sun-screening cream.

7. A method for preparing an external composition for skin which comprises obtaining an extract of a white bacterium of the genus Sphingomonas, and mixing said extract with a cosmetically acceptable carrier.

8. A method for preparing an external composition for skin according to claim 7 wherein said extract is not subject to a decoloring process.

9. A method for preparing an external composition for skin according to claim 7 which comprises the steps of washing the white bacterium of the genus Sphingomonas with acetone and then extracting the resultant with alcohol or alcohol-water mixture.

10. A method for preparing an external composition for skin according to claim 9 wherein said alcohol or alcohol-water mixture is methanol, propanol-water mixture or butanol-water mixture.

11. A method for preparing an external composition for skin according to claim 10 wherein said alcohol or alcohol-water mixture is propanol-water mixture having a propanol content of 75 wt % or less, or butanol-water mixture having a butanol content of 95 wt % or less.

12. A method for preparing an external composition for skin according to claim 11 wherein said alcohol or alcohol-water mixture is butanol-water mixture having a butanol content ranging from 80 to 95 wt %.

13. A method for preparing an external composition for skin according to claim 7 wherein said external composition comprises a shingoglycolipid represented by the following formula:

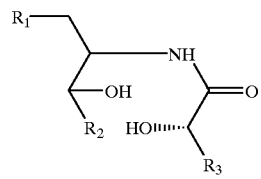

where $R_1$ represents a sugar portion consisting of a single uronic acid or one to four hexoses selected from a group consisting of uronic acid, glucosamine, galactose and mannose; $R_2$ represents an alkyl group which may have a cycloalkyl group, an alkenyl group or an alkynyl group; and $R_3$ represents an alkyl group; these alkyl, alkenyl and alkynyl groups being straight or branched, and substituted or unsubstituted.

14. A method for preparing an external composition for skin according to claim 13 wherein said $R_1$ consists of 3 or 4 hexoses.

15. A method for preparing an external composition for skin according to claim 14 wherein said $R_1$ is a sugar portion of four hexoses consisting of a uronic acid, a glucosamine, a galactose and a mannose; three hexoses consisting of a uronic acid, a glucosamine and a galactose; or four hexoses consisting of a uronic acid, a galactose and two glucoses.

16. A method for preparing an external composition for skin according to claim 13 wherein said $R_1$ is represented by any one of the following formulae A to D:

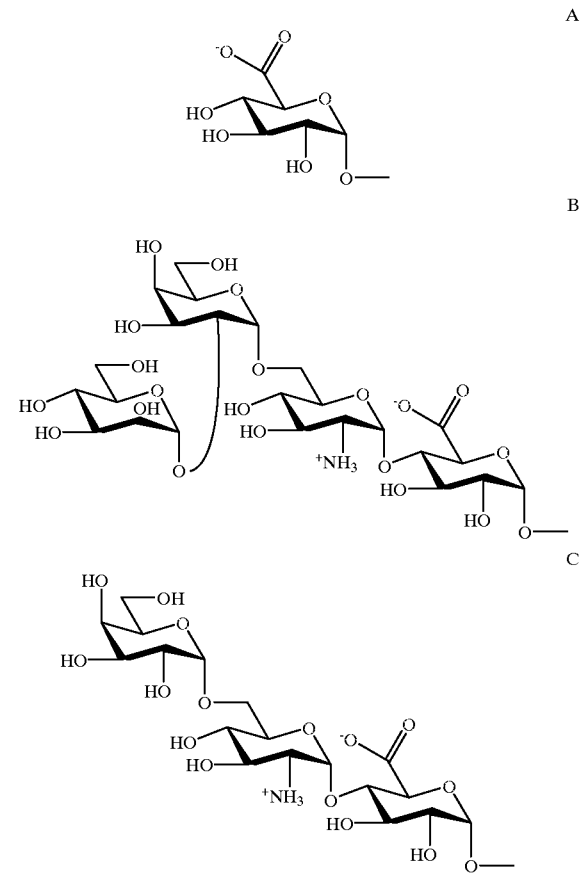

-continued

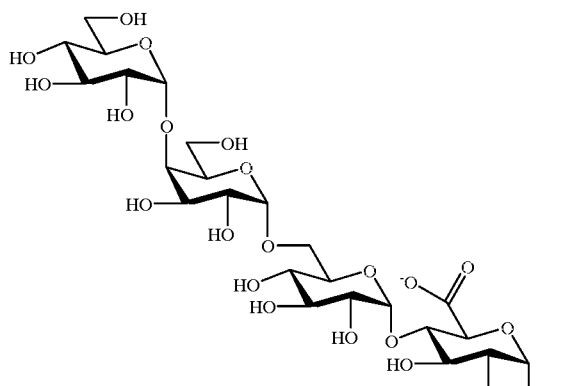
D

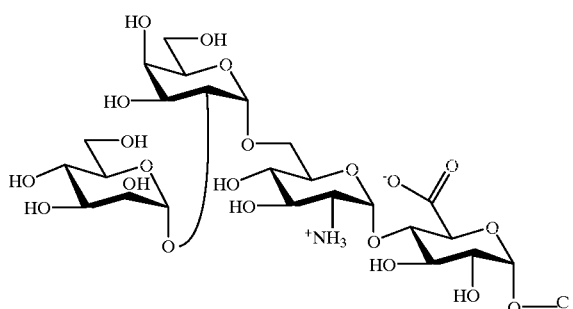
B

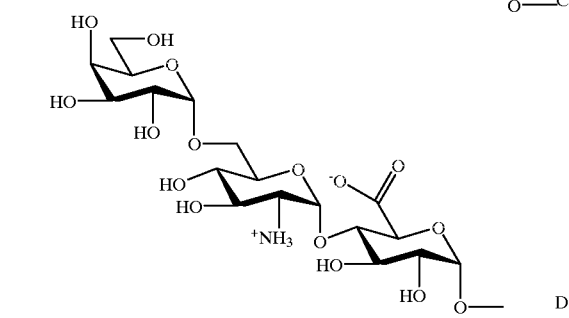

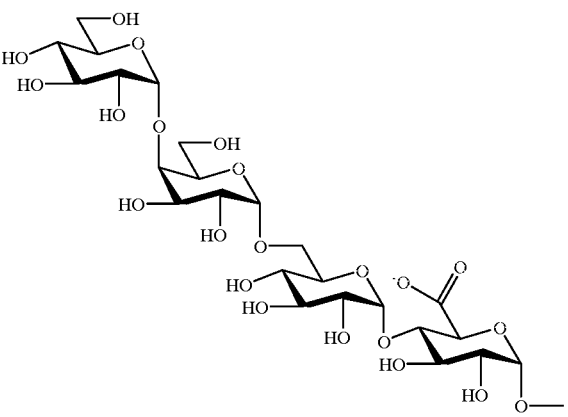
D

17. A method for preparing an external composition for skin according to claim 1 wherein said $R_2$ has 15 to 25 carbon atoms.

18. A method for preparing an external composition for skin according to claim 17 wherein said $R_2$ has a structure represented by any one of the following formulae a to c:

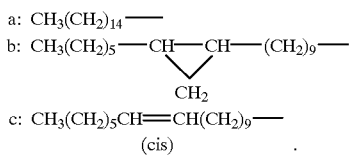

19. A method for preparing an external composition for skin according the claim 13 wherein said $R_3$ is a substituted or unsubstituted straight alkyl group having 10 to 20 carbon atoms.

20. A method for preparing an external composition for skin according to claim 17 wherein said $R_3$ is a straight alkyl group having 12 carbon atoms.

21. A method for preparing an external composition for skin according to claim 7 which further comprises the step of mixing said extract with at least one of whitening agent, surfactant, dye, perfumery, aseptic agent, pigment, mildew-proof agent, antioxidant, UV absorber, infrared absorber, fluorescent material, metal ion blocker, binder, filler, antiphlogistic, circulation accelerator, cell activator and antibiotic.

22. A method for preparing an external composition for skin according to claim 13 wherein said $R_1$ has a structure represented by any one of the following formulae A to D:

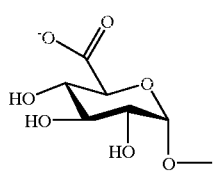
A and said $R_2$ has a structure represented by any one of the following formulae a to c:

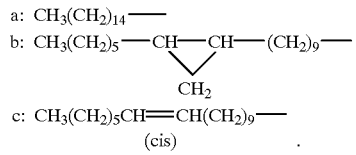

23. A method of using the external composition for skin prepared by the method according to claim 7 as a toilet soap, shampoo, cleansing foam, rinse, eye cream, eye shadow, cream or milky lotion, toilet lotion, perfume, face powder, facial oil, hair-care cosmetics, hair dye, jelly fragrance, powder, pack, shaving cream, shaving lotion, suntan oil, anti-suntan oil, suntan lotion, sun-screening lotion, suntan cream, sun-screening cream, foundation, powdery fragrance, cheek rouge, mascara, eyebrow pencil, nail cream, nail enamel, nail enamel remover, hair cleaner, bath cosmetics, lipstick, lip cream, eyeliner, toothpaste, deodorant agent eau de cologne, hair tonic, hair restorer, ointment, wet pack, medicated lip cream or anti-atopic agent, comprising
applying said composition to skin, hair or fingernails.

* * * * *